(12) United States Patent
White, Jr. et al.

(10) Patent No.: US 9,301,764 B2
(45) Date of Patent: Apr. 5, 2016

(54) OCCLUDING DEVICE AND METHOD OF OCCLUDING FLUID FLOW THROUGH A BODY VESSEL

(75) Inventors: Robert I. White, Jr., Branford, CT (US); Thomas A. Osborne, Bloomington, IN (US); Kurt J. Tekulve, Ellettsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 2431 days.

(21) Appl. No.: 10/884,728

(22) Filed: Jul. 2, 2004

(65) Prior Publication Data

US 2005/0004598 A1    Jan. 6, 2005

Related U.S. Application Data

(60) Provisional application No. 60/485,306, filed on Jul. 3, 2003.

(51) Int. Cl.
*A61B 17/12* (2006.01)

(52) U.S. Cl.
CPC ....... *A61B 17/12022* (2013.01); *A61B 17/1215* (2013.01); *A61B 17/12109* (2013.01); *A61B 17/12113* (2013.01); *A61B 17/12145* (2013.01); *A61B 2017/1205* (2013.01)

(58) Field of Classification Search
CPC ................... A61B 17/12022; A61B 17/12109; A61B 17/12113; A61B 17/1214; A61B 17/12145; A61B 17/1215
USPC ............... 606/200, 151, 108, 213; 623/23.74, 623/1.11–1.13, 23.72; 128/831, 833, 841, 128/887
See application file for complete search history.

(56) References Cited

U.S. PATENT DOCUMENTS

| | | | |
|---|---|---|---|
| 4,561,439 A | | 12/1985 | Bishop et al. |
| 4,957,501 A | | 9/1990 | Lahille et al. |
| 4,994,069 A | * | 2/1991 | Ritchart et al. ............... 606/191 |
| 5,263,964 A | | 11/1993 | Purdy |
| 5,382,260 A | * | 1/1995 | Dormandy et al. ........... 606/151 |
| 5,413,586 A | | 5/1995 | Dibie et al. |
| 5,417,708 A | | 5/1995 | Hall et al. |
| 5,423,829 A | * | 6/1995 | Pham et al. .................... 606/108 |
| 5,476,472 A | * | 12/1995 | Dormandy et al. ........... 606/151 |
| 5,527,338 A | | 6/1996 | Purdy |
| 5,531,788 A | | 7/1996 | Dibie et al. |
| 5,562,698 A | | 10/1996 | Parker |
| 5,669,931 A | * | 9/1997 | Kupiecki et al. ............... 606/191 |
| 5,690,667 A | | 11/1997 | Gia |
| 5,690,671 A | * | 11/1997 | McGurk et al. ............... 606/200 |
| 5,693,067 A | | 12/1997 | Purdy |
| 5,695,518 A | | 12/1997 | Laerum |
| 5,707,053 A | * | 1/1998 | Plunkett et al. .................. 269/49 |
| 5,725,534 A | | 3/1998 | Rasmussen |
| 5,749,894 A | * | 5/1998 | Engelson ....................... 606/213 |
| 5,766,160 A | * | 6/1998 | Samson et al. ..................... 606/1 |
| 5,792,154 A | * | 8/1998 | Doan et al. .................... 606/151 |

(Continued)

FOREIGN PATENT DOCUMENTS

WO    WO 98/09570    *   3/1998

*Primary Examiner* — Kathleen Holwerda
(74) *Attorney, Agent, or Firm* — Brinks Gilson & Lione

(57) ABSTRACT

An occluding device for occluding fluid flow through a lumen of a body vessel. The device comprises a coil and fibers attached to the coil. The coil has about 5 to 60 grams of initial tension to facilitate the coil to fold when deployed. The fibers extend from the coil at a length.

24 Claims, 9 Drawing Sheets

(56) References Cited

U.S. PATENT DOCUMENTS

| | | | |
|---|---|---|---|
| 5,797,953 A | 8/1998 | Tekulve | |
| 5,830,230 A | 11/1998 | Berryman et al. | |
| 5,855,578 A * | 1/1999 | Guglielmi et al. | 606/32 |
| 5,893,869 A | 4/1999 | Barnhart et al. | |
| 5,895,391 A | 4/1999 | Farnholtz | |
| 5,895,398 A | 4/1999 | Wensel et al. | |
| 5,911,717 A | 6/1999 | Jacobsen et al. | |
| 5,925,062 A | 7/1999 | Purdy | |
| 5,935,145 A * | 8/1999 | Villar et al. | 606/191 |
| 5,972,019 A | 10/1999 | Engelson et al. | |
| 6,015,424 A | 1/2000 | Rosenbluth et al. | |
| 6,024,765 A | 2/2000 | Wallace et al. | |
| 6,086,577 A | 7/2000 | Ken et al. | |
| 6,093,199 A | 7/2000 | Brown et al. | |
| 6,117,157 A | 9/2000 | Tekulve | |
| 6,126,672 A | 10/2000 | Berryman et al. | |
| 6,136,015 A * | 10/2000 | Kurz et al. | 606/191 |
| 6,143,007 A * | 11/2000 | Mariant et al. | 606/151 |
| 6,156,061 A | 12/2000 | Wallace et al. | |
| 6,165,198 A | 12/2000 | McGurk et al. | |
| 6,187,024 B1 * | 2/2001 | Boock et al. | 606/191 |
| 6,254,592 B1 | 7/2001 | Samson et al. | |
| 6,277,125 B1 | 8/2001 | Barry et al. | |
| 6,277,126 B1 | 8/2001 | Barry et al. | |
| 6,331,184 B1 | 12/2001 | Abrams | |
| 6,340,364 B2 | 1/2002 | Kanesaka | |
| 6,358,228 B1 | 3/2002 | Tubman et al. | |
| 6,361,547 B1 | 3/2002 | Hieshima | |
| 6,379,374 B1 | 4/2002 | Hieshima et al. | |
| 6,383,174 B1 | 5/2002 | Eder | |
| 6,428,557 B1 | 8/2002 | Hilaire | |
| 6,432,122 B1 | 8/2002 | Gilson et al. | |
| 6,436,112 B2 | 8/2002 | Wensel et al. | |
| 6,458,137 B1 | 10/2002 | Klint | |
| 6,530,935 B2 | 3/2003 | Wensel et al. | |
| 6,537,293 B1 | 3/2003 | Berryman et al. | |
| 6,544,275 B1 | 4/2003 | Teoh | |
| 6,551,340 B1 * | 4/2003 | Konya et al. | 606/191 |
| 6,554,849 B1 | 4/2003 | Jones et al. | |
| 6,613,074 B1 | 9/2003 | Mitelberg et al. | |
| 6,656,201 B2 * | 12/2003 | Ferrera et al. | 606/191 |
| 6,776,788 B1 | 8/2004 | Klint et al. | |
| 2001/0007947 A1 | 7/2001 | Kanesaka | |
| 2001/0020175 A1 | 9/2001 | Yassour et al. | |
| 2001/0031980 A1 | 10/2001 | Wensel et al. | |
| 2002/0016609 A1 | 2/2002 | Wensel et al. | |
| 2002/0072764 A1 | 6/2002 | Sepetka et al. | |
| 2002/0138096 A1 | 9/2002 | Hieshima | |
| 2003/0004542 A1 | 1/2003 | Wensel et al. | |
| 2003/0009191 A1 | 1/2003 | Wensel et al. | |
| 2003/0014072 A1 | 1/2003 | Wensel et al. | |
| 2003/0040772 A1 | 2/2003 | Hyodoh et al. | |
| 2003/0097094 A1 | 5/2003 | Ouriel et al. | |
| 2003/0120302 A1 | 6/2003 | Minck, Jr. et al. | |
| 2003/0212427 A1 | 11/2003 | Truckai et al. | |

* cited by examiner

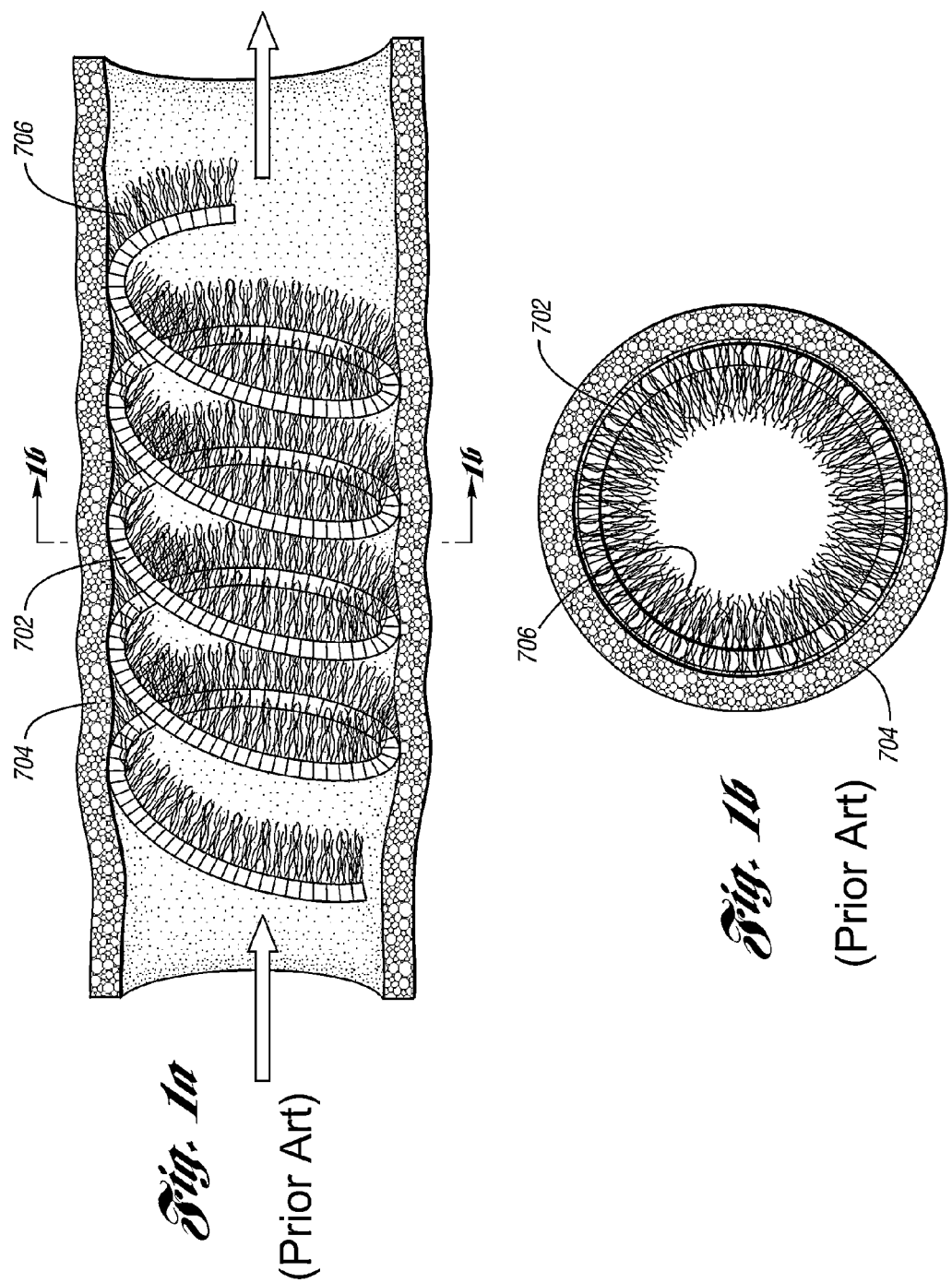

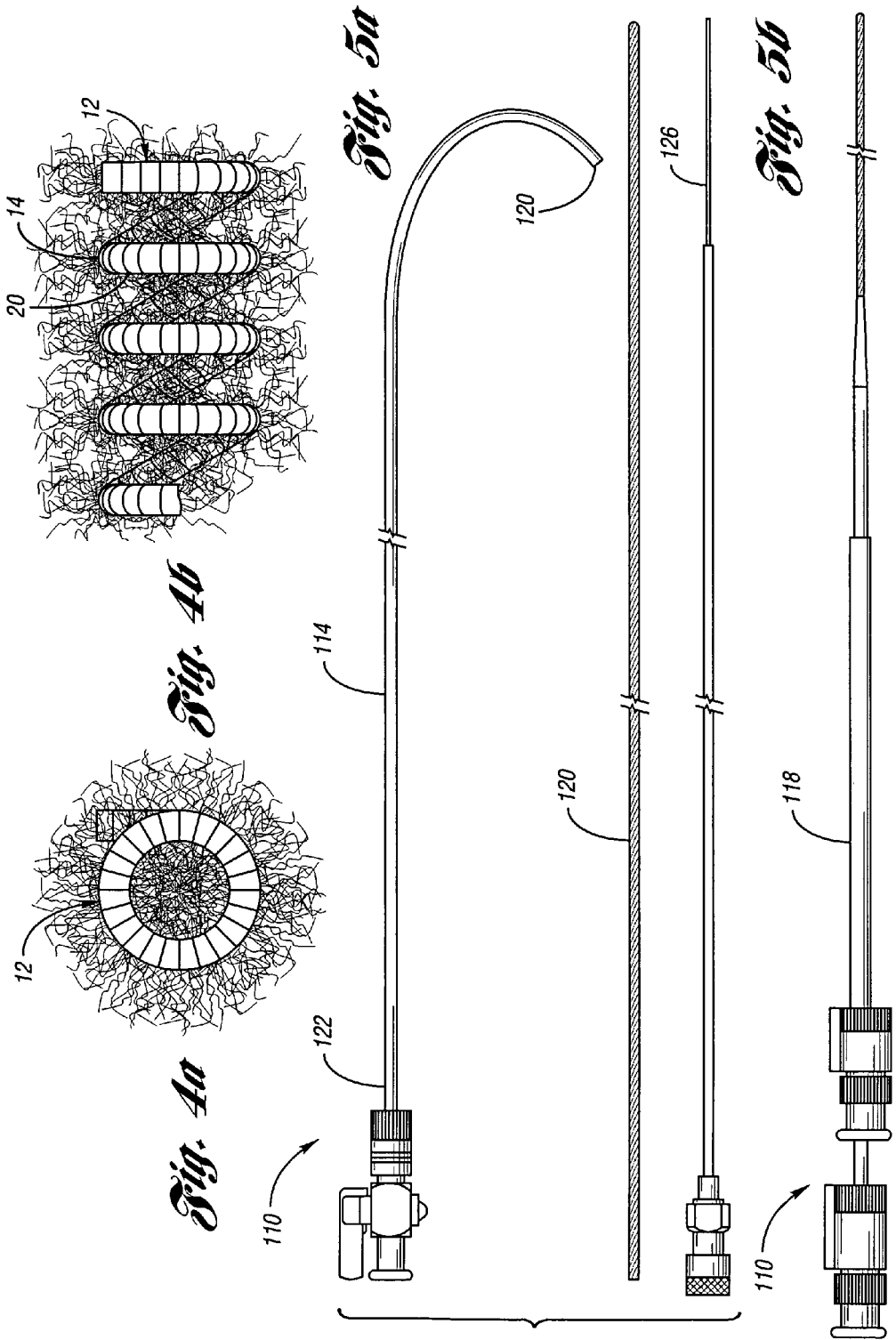

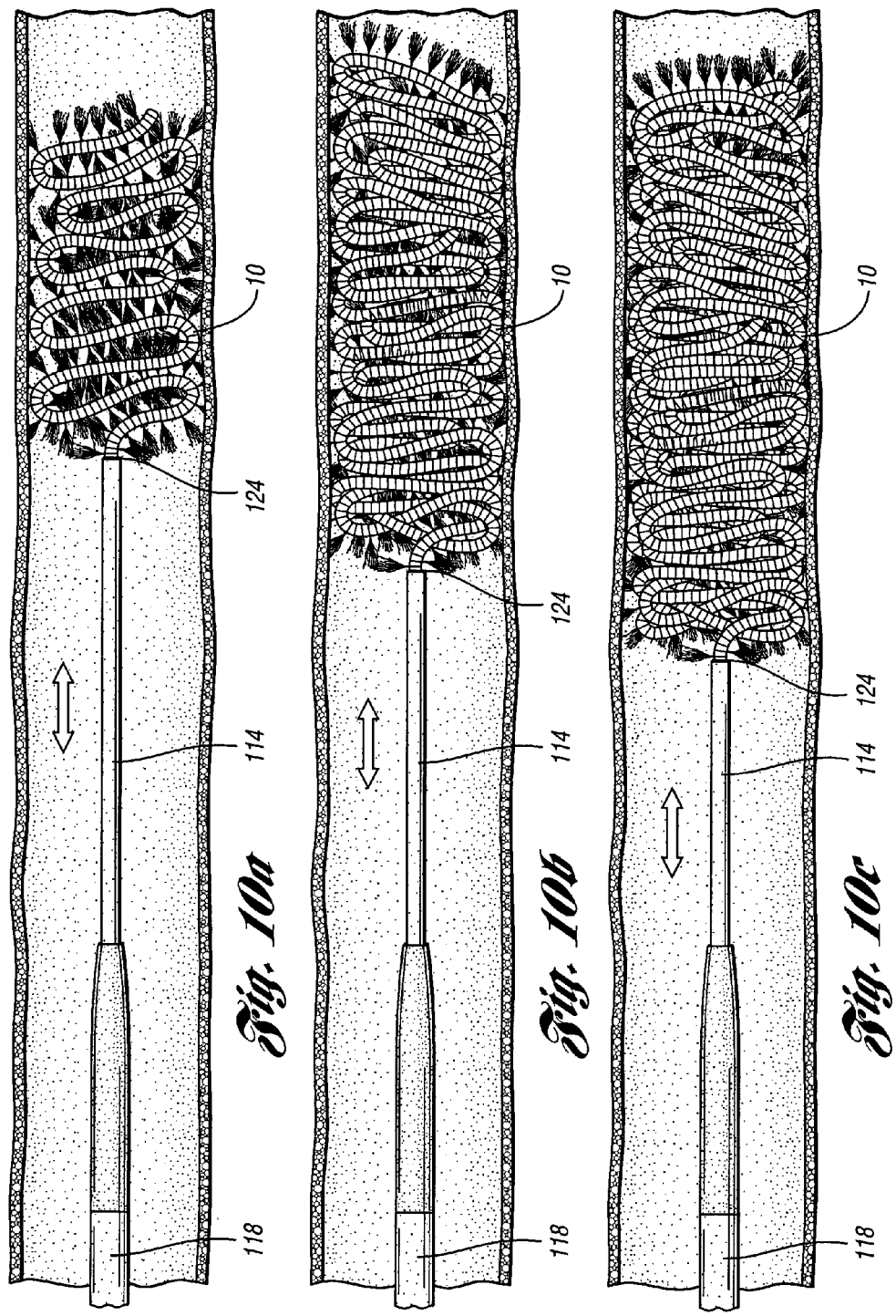

OCCLUDING DEVICE AND METHOD OF OCCLUDING FLUID FLOW THROUGH A BODY VESSEL

CROSS-REFERENCE TO RELATED APPLICATIONS

This application claims priority to U.S. Provisional Application No. 60/485,306 filed Jul. 3, 2003, entitled "Occluding Device and Method of Occluding Fluid Flow Through A Body Vessel."

BACKGROUND OF THE INVENTION

1. Field of Invention

The present invention relates to medical devices. More particularly, the invention relates to occluding devices and methods of occluding fluid flow through a body vessel.

2. Background of the Invention

Pushable fibered coils have been used as a primary occluding device for treatment of various arteriovenous malformations (AVM) and varicoceles, as well as for many other arteriovenous abnormalities in the body. Occluding devices are also used to repair abnormal shunts between arteries and veins, prevent or reduce blood flow to tumors, stop hemorrhaging as a result of trauma, and stabilize aneurysms to prevent rupture. Pushable fibered coils may be configured in a variety of sizes with varying diameters and may be made of several different materials including stainless steel and platinum.

Although current pushable fibered coils are adequate, such coils may be improved for more effective occlusion of fluid flow through a lumen of a body vessel. Many medical procedures for occluding blood flow through an artery or vein require a number of coils, since a single coil or two may not be sufficient to effectively occlude blood flow through a lumen of an artery or vein. In many current procedures, many coils may be packed within each other to produce effective cross sectional occlusion of fluid flow through a body vessel. In some instances, these procedures may involve an undesirable amount of additional time and costs.

Many pushable fibered coils are designed with high tension or stiffness, e.g., between about 60 to 100 weight grams, to wedge or attach strands of fiber to the coils. Upon deployment in a body vessel for occlusion, such coils tend to reform or recanalize back to its helical shape because of the high tension. The helical shape of the coils creates an undesirable opening through which fluid may flow, thereby requiring additional coils to be deployed in the body vessel.

For example, prior art FIGS. 1a-1d depict typical prior art coils. FIG. 1a shows a prior art coil 702 deployed in a body vessel 704 for treatment of various AVM and varicoceles and other arteriovenous abnormalities. Prior art coil 702 has a relatively high initial tension, e.g. greater than 60 weight grams, which contributes to reformation of the coil 702 back to its helical shape in the vessel 704. As depicted in FIG. 1b, the strands 706 of fiber attached to the coil 702 are concentrated around the periphery of the vessel 704. Rather than occlusion, the vessel 704 only experiences a reduced lumen through which blood may still flow, requiring further embolotherapy. As a result, more occluding devices are added until the lumen is filled or occluded.

Prior art FIG. 1c is a pulmonary angiogram 710 in the arterial phase and prior art FIG. 1d is a pulmonary angiogram 720 in the venous phase, each depicting conventional coils 712 and 714 in the pulmonary vasculature 716 after an initial embolotherapy procedure of a pulmonary AVM. Conventional coils 712 and 714 are made of stainless steel and have a relatively high initial tension. As shown, conventional coils 712 and 714 have reformed back and re-opened to their helical shape after the initial procedure, allowing blood flow through the coil in the blood vessel. In this example, further embolotherapy is recommended to occlude the vessel.

Due to the short length of pushable fibered coils, a practitioner may experience difficulty in accurately deploying a coil at a desired location in a body vessel. Pushable fibered coils are short in length, e.g., 2 to 4 centimeters. During deployment, the coil contacts the wall of a body vessel to be occluded. Upon contact with the wall, the coil typically becomes fully deployed from a catheter in the body vessel, thereby preventing the practitioner from adjusting the location of the coil.

Additionally, due to the short length of pushable fibered coils, there is a concern that current coils are difficult to advance through a catheter. A pushable fibered coil has fibers packed along the length of the coil. Due to its short length, the fibers fold or bend over each other when the coil is loaded in a catheter. As a result, the coil has an enlarged diameter to be advanced through the catheter, thereby creating an undesirable resistance to the practitioner.

BRIEF SUMMARY OF THE INVENTION

The present invention provides an improved occluding device and an improved method of occluding fluid flow through a lumen of a body vessel. The occluding device comprises a coil member that is designed with low initial tension. In one embodiment, the coil member is an extension or elongating spring. The low initial tension of the coil facilitates the coil member to be folded across the lumen during deployment from a catheter. In one embodiment, initial tension is defined to be the amount of force required to cause a 4 centimeter length of coil to begin to elongate or the amount of force required to cause a coil to begin elongating at a ratio of between about 1.25 to 15 grams per centimeter. The occluding device is designed to tend to resist reformation back to its original helical shape after deployment. When deployed in a lumen of a body vessel, the occluding device has improved efficiency, thereby minimizing or eliminating the need for a number of coils used during embolotherapy.

Additionally, the occluding device has an extended length, e.g., between about 3 to 20 centimeters (cm), and preferably about 14 (cm), to accommodate a practitioner for improved accuracy when deploying the occluding device. With the extended length of the occluding device, fibers may be attached therealong, avoiding an enlarged diameter of the occluding device when loaded in a catheter. With the extended length of the occluding device, the fibers are able to be spaced apart from each other and are held between loops of the coil member by the initial tension of the coil member. The fibers include strands comprised of a synthetic polymer such as a polyester textile fiber. In one embodiment, the strands are spaced apart from each other by at least one loop along the extended length of the coil member, avoiding an enlarged diameter that otherwise would have been created when folding the strands over each other during loading in a catheter. Thus, undesirable resistance may be avoided when deployed the occluding device from a catheter.

In one embodiment, the occluding device comprises a coil having about 5 to 60 grams of initial tension to facilitate the coil to fold when deployed. The coil also has fibers attached thereto and extending therefrom.

In another embodiment, device comprises a primary coil formed in a secondary coil. The primary coil has a ratio of between about 1.25 to 15 grams per centimeter of initial tension to the secondary coil to facilitate the primary coil to be folded across the lumen of the body vessel when deployed. The device further comprises fibers attached to the primary coil and extending therefrom.

The present invention further provides a method of occluding fluid flow through a lumen of a body vessel. The method includes deploying a first portion of an occluding device at a desired point of occlusion in the body vessel and ascertaining the position of the first portion relative to the desired point of occlusion in the body. The method further includes folding a remaining portion of the occluding device with the first portion to pack the loops together to occlude the lumen, if the first portion is at the desired point of occlusion in the body.

The present invention further provides another method of occluding fluid flow through a lumen of a body vessel. In one embodiment, the method includes deploying a first portion of the occluding device at a desired point of occlusion in the body vessel and ascertaining the position of the first portion at the desired point of occlusion in the body. The method further includes deploying the remaining portion of the occluding device to pack loops of the occluding device together to occlude a cross-sectional lumen of the coil, if the first portion is at the desired point of occlusion in the body vessel.

The present invention also includes an embolization kit for occluding fluid flow through a body vessel. The kit comprises a guide catheter and a microcatheter having proximal and distal ends. The microcatheter is configured to be passed through the guide catheter to position the microcatheter in the body vessel. The microcatheter has a hub adjacent the proximal end. The kit further includes an occluding device. The occluding device comprises a coil having about 5 to 60 grams of initial tension to facilitate the coil to fold when deployed. The occluding device further comprises fibers attached to the coil and extending therefrom.

The present invention provides another embodiment of a body vessel embolization kit for occluding fluid flow through a lumen of a body vessel. In this embodiment, the kit comprises a microcatheter having proximal and distal ends and defining a lumen. The kit further comprises an occluding device including a coil and fibers attached to the coil. The coil has about 5 to 60 grams of initial tension to facilitate the coil to fold when deployed. The fibers extend from the coil.

Further objects, features and advantages of the invention will become apparent from consideration of the following description and the appended claims when taken in connection with the accompanying drawings.

BRIEF DESCRIPTION OF THE DRAWINGS

FIG. 1a is a side view of a prior art coil deployed in a body vessel;

FIG. 1b is a cross-sectional view of the prior art coil taken along line 1b-1b in FIG. 1a;

FIG. 4a is a cross-sectional view of the occluding device of FIG. 1 taken along line 4a-4a;

FIG. 4b is an enlarged view of the occluding device in area 4b of FIG. 1;

FIG. 5a is an exploded view of an embolization kit for one embodiment of the occluding device of the present invention;

FIG. 5b is a side view of the embolization kit;

FIG. 6c is a cross-sectional view of the occluding device in FIG. 6a;

FIG. 7d is a renal angiogram depicting the occluding device in FIG. 7c and a conventional occluding device;

FIGS. 10a-10c are side views of one embodiment of an embolization kit used to implement methods depicted in FIGS. 8 and 9.

DETAILED DESCRIPTION OF THE INVENTION

The following provides a detailed description of currently preferred embodiments of the present invention. The description is not intended to limit the invention in any manner, but rather serves to enable those skilled in the art to make and use the invention.

The present invention generally provides an occluding device used for transcatheter embolization. The occluding device is preferably used to occlude fluid flow through a lumen of a body vessel such as for an occlusion of an arteriovenous malformation (AVM). The occluding device comprises a primary coil having a relatively low initial tension. The primary coil is formed in a helical shape to define a secondary coil. The occluding device may be made of any suitable material, and is preferably made of platinum for its radiopacity.

The initial tension of the primary coil provides an ability for the occluding device to fold when deployed from a catheter. The occluding device preferably includes fibers wedged or attached between loops of the primary coil and extending therefrom. When the occluding device is deployed in a lumen of a body vessel, the fibers help to occlude fluid flow through the lumen of the body vessel.

The occluding device also may be used for treatment of renal AVM, pulmonary AVM, vascular tumors, low-flow fistulas, trauma related hemorrhages, and visceral vasculature defects including varicoceles, aneurysms, and selected telangiectasias. For example, treatment of visceral vasculature defects may include but are not limited to embolotherapy on gastroduodenal hemorrhages, hepatic aneurysms, celiac aneurysms, internal iliac aneurysms, and internal spermatic varicoceles.

Figure 2A:
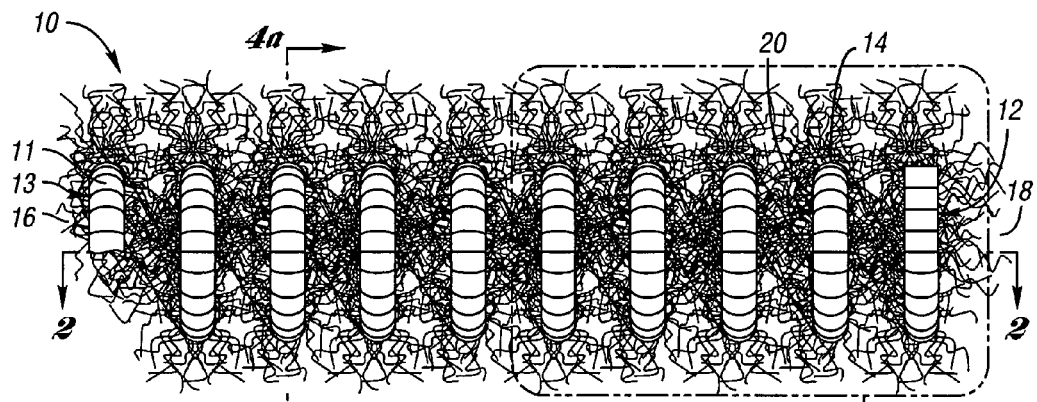
FIG. 2a is a side view of an occluding device in accordance with one embodiment of the present invention.
Figure 2B:
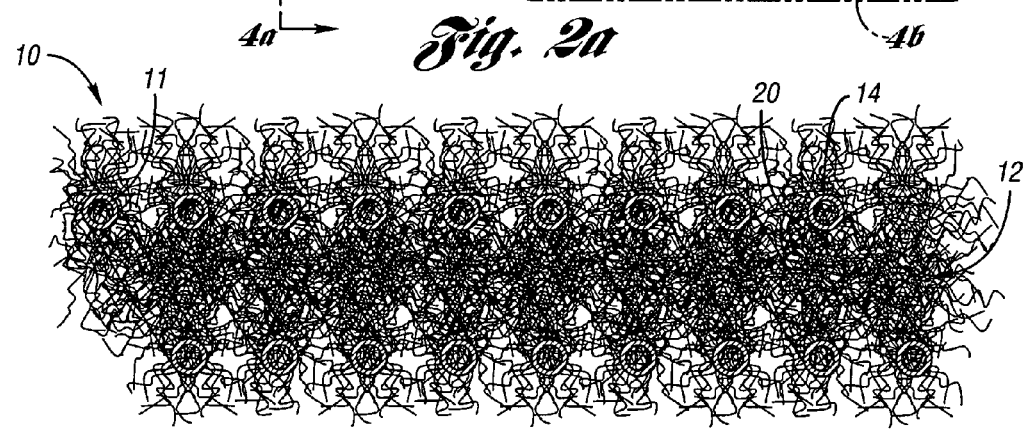
FIG. 2b is a cross-sectional view of the occluding device of FIG. 1 taken along line 2-2.
Figure 3A:
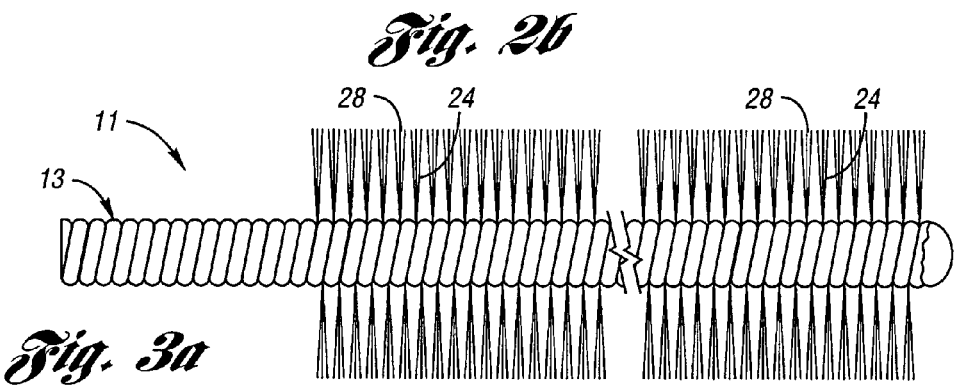
FIG. 3a is a side view of a primary coil in FIG. 1 depicting the occluding device in an uncoiled length.
Figure 3B:
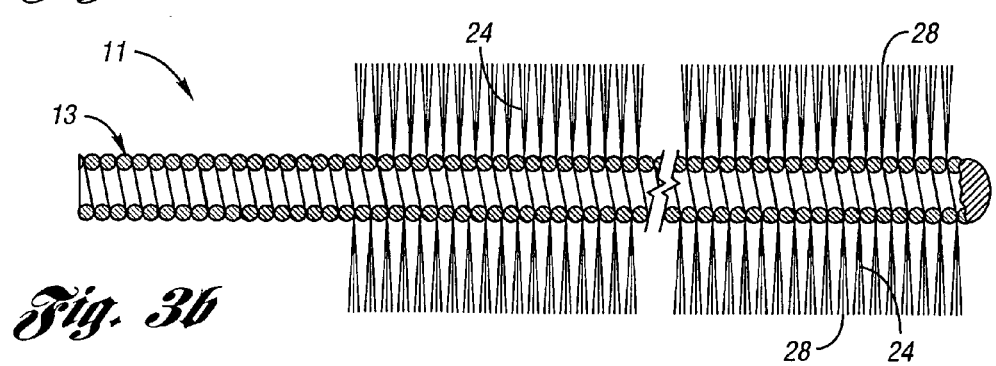
FIG. 3b is a cross-sectional view of the primary coil in FIG. 3a taken along line 3b-3b.

FIG. 2a illustrates an occluding device 10 for occlusion of fluid flow through a lumen of a body vessel in accordance with one embodiment of the present invention. As shown in FIGS. 2a through 3b, the occluding device 10 comprises a primary coil 11 formed in a secondary coil 12. Preferably, the primary coil 11 is formed to define a primary body 13. As shown in FIGS. 2a and 2b, the primary body 13 is formed, preferably by a coil winding machine, to a helical shape to define a secondary coil 12. The secondary coil 12 includes a series of loops 20 of a secondary body 14 having a first end 16 and a second end 18. The series of loops 20 define a cross-sectional lumen formed axially along the coil 12. Preferably, the occluding device 10 further includes fibers 24 attached to the loops 20 of the coil 12.

Preferably, the primary coil 11 comprises platinum or any other suitable metal, composition, or alloy having between about 50,000 and 350,000 pounds per square inch tensile strength. It has been determined that the tensile strength range described above provides the coil with the capability of being flexible, malleable, and folded.

The coil 11 has an initial tension of between about 5 to 60 grams of weight, and preferably between about 10 to 30 grams of weight. Initial tension may be defined to be the amount of force required to cause a 4 centimeter length of coil to begin to elongate. The initial tension may also be defined by the amount of force required to cause a coil to begin elongating at a ratio of between about 1.25 to 15 grams per centimeter, and preferably between about 2.5 to 7.5 grams per centimeter. Without limiting the invention, it is believed that the initial tension of the coil provide the occluding device the capability of being folded across the diameter of a lumen of a body vessel after deployment from a catheter.

The coil 11 may be made by any apparatus known in the art. For example, the coil may be made by any commercial coil winding machine such as a roller deflecting apparatus, a mandrel apparatus, or any other suitable means.

In this embodiment, the coil 11 may have a length of between about 3 to 20 centimeters. As shown in FIG. 4a, the coil 12 may have an outer diameter ranging between about 3 to 15 millimeters. The primary coil 11 may have an outer diameter of between about 0.010 and 0.035 inch. The catheter inner diameter through which the occlusion device may be advanced ranges between about 0.014 to 0.027 inch.

FIGS. 2a and 4b illustrate the helical body 14 of the coil 12 having a series of connected loops 20 axially spaced apart by a predetermined distance. In this embodiment, the predetermined distance of up to 4 millimeters curl space. Curl space is defined as the distance between two loops 20 of coil 12.

As shown in FIGS. 2a-b and 3a-b, the occluding device 10 further comprises fibers 24 wedged or attached to the coil 11 and extending therefrom. The fibers 24 are spaced apart from each other and are held between loops of the coil 11 by the initial tension of the coil 11. Preferably, the fibers 24 include strands 28 comprised of a synthetic polymer such as a polyester textile fiber, e.g., DACRON™. As desired, the strands may be wedged between alternating loops, alternating double loops, or any desired configuration. The strands 28 being held spaced apart from each other along the extended length of the coil 11, e.g., 14 centimeters, avoid an enlarged diameter created when fibers fold or bend over each other when the coil is loaded in a catheter. As a result, an undesirable resistance is avoided when the coil 12 is advanced through the catheter.

Preferably, the strands 28 have a length extending from the coil 11 of between about 3 to 8 millimeters. In an application the strands may have between about 5 to 6 millimeters as desired. In this embodiment, the fibers 24 are spaced apart from each other by about 1 to 3 millimeters. Preferably, the strands 28 have an outer diameter of about 0.00050 to 0.00100 inch.

During deployment of the occluding device 10, the low initial tension of the coil 11 is capable of being folded across the lumen of a body vessel to be occluded.

When the device 10 is deployed from a catheter, the low initial tension of the primary coil provides the primary coil the capability of being folded across the lumen of a body vessel for cross-sectional occlusion. In this embodiment, when the primary coil is folded with the strands 28, the occluding device 10 is in a "packed" or "nested" state a length of about 5% or more of the original length of the primary coil 11. When packed, the occluding device 10 provides a relatively tightly nested, dense mass that effectively occludes fluid flow though a lumen of a body vessel.

Figure 6A:
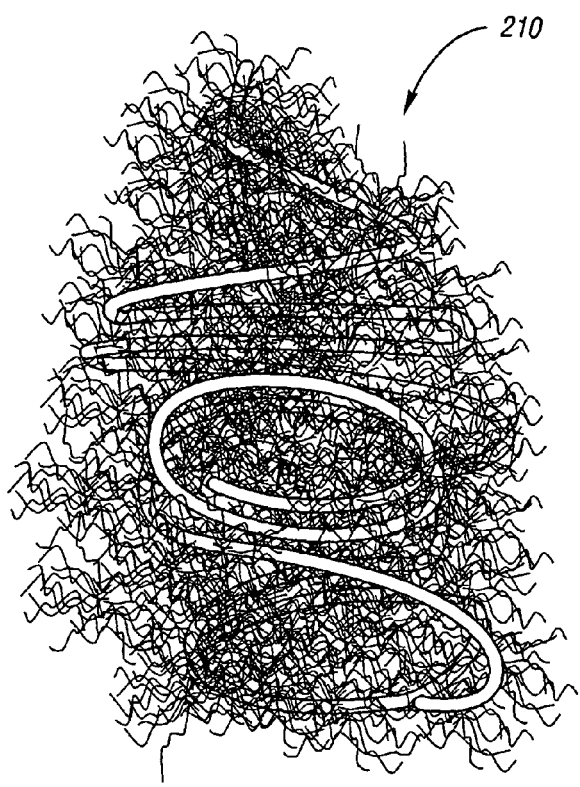
FIG. 6a is a side view of a occluding device in a packed state.

FIG. 6a depicts an occluding device 210 in a packed state wherein the primary coil and strands are folded across the diameter of the secondary coil. As shown, the primary coil and the strands are packed with each other for occluding fluid flow through a lumen of a body vessel.

Figure 6C:
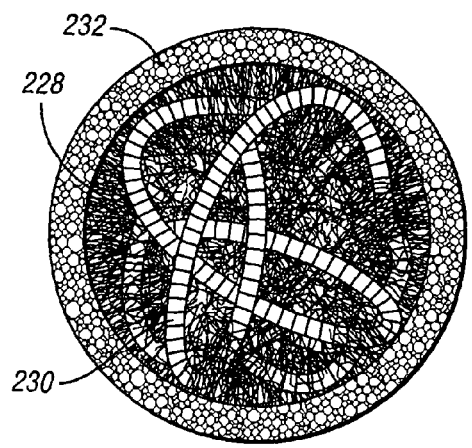
Figure 6B:
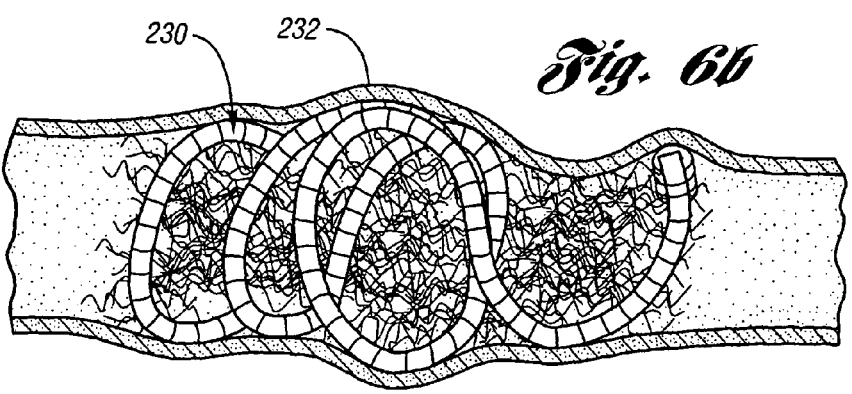
FIG. 6b is a side cross-sectional environmental view of a packed occluding device deployed in a body vessel.

FIGS. 6b and 6c illustrate an environmental view of an occluding device 230 with attached strands 228 deployed within a body vessel 232 for occlusion of blood flow therethrough. The relatively low initial tension of the coil 230 allows the coil to be folded back and forth across the lumen of the vessel 232 in a packed state. In the packed state, the folding of the coil 230 serves to fill or occlude the cross-sectional area of the vessel 232 with embolus. The relatively low initial tension of the coil 230 allows the coil to maintain its packed configuration, avoiding reformation back to its helical shape.

FIGS. 5a and 5b depict a body vessel embolization kit 110 which implements the occluding device in accordance with one embodiment of the present invention. As shown, the kit 110 includes a microcatheter 114 defining a catheter lumen and preferably made from a soft, flexible material such as silicone or any other suitable material. Generally, the microcatheter 114 has a proximal end 122, a distal end 124, and a plastic adapter or hub 116 to receive apparatus to be advanced therethrough. In this embodiment, the inside diameter of the microcatheter may range between 0.014 and 0.027 inch. The kit 110 further includes a guide wire 120 which provides the guide catheter 118 a path during insertion of the guide catheter 118 within a body vessel. The size of the wire guide is based on the inside diameter of the guide catheter.

In this embodiment, the kit 110 further includes a polytetrafluoroethylene (PTFE) guide catheter or sheath 118 for percutaneously introducing the microcatheter 114 in a body vessel. Of course, any other suitable material may be used without falling beyond the scope or spirit of the present invention. The guide catheter 118 may have a size of about 4-French to 8-French and allows the microcatheter 114 to be inserted therethrough to a desired location in the body vessel. The guide catheter 118 receives the microcatheter 114 and provides stability of the microcatheter 114 at a desired location of the body vessel. For example, the guide catheter 118 may stay stationary within a common visceral artery, e.g., a common hepatic artery, and add stability to the microcatheter 114 as the microcatheter is advanced through the guide catheter to a point of occlusion in a connecting artery, e.g., the left or right hepatic artery.

When the distal end 124 of the microcatheter 114 is at the point of occlusion in the body vessel, the occluding device is loaded at the proximal end 122 of the microcatheter 114 and is advanced through the microcatheter for deployment through the distal end 124. In this embodiment, a push wire 126 is used to mechanically advance or push the occluding device through the microcatheter 114. The size of the push wire used depends on the diameters of the microcatheter.

It is to be understood that the body vessel embolization kit 110 described above is merely one example of a kit that may be used to deploy the occluding device in a body vessel. Of course, other kits, assemblies, and systems may be used to deploy any embodiment of the occluding device without falling beyond the scope or spirit of the present invention.

Figure 7B:
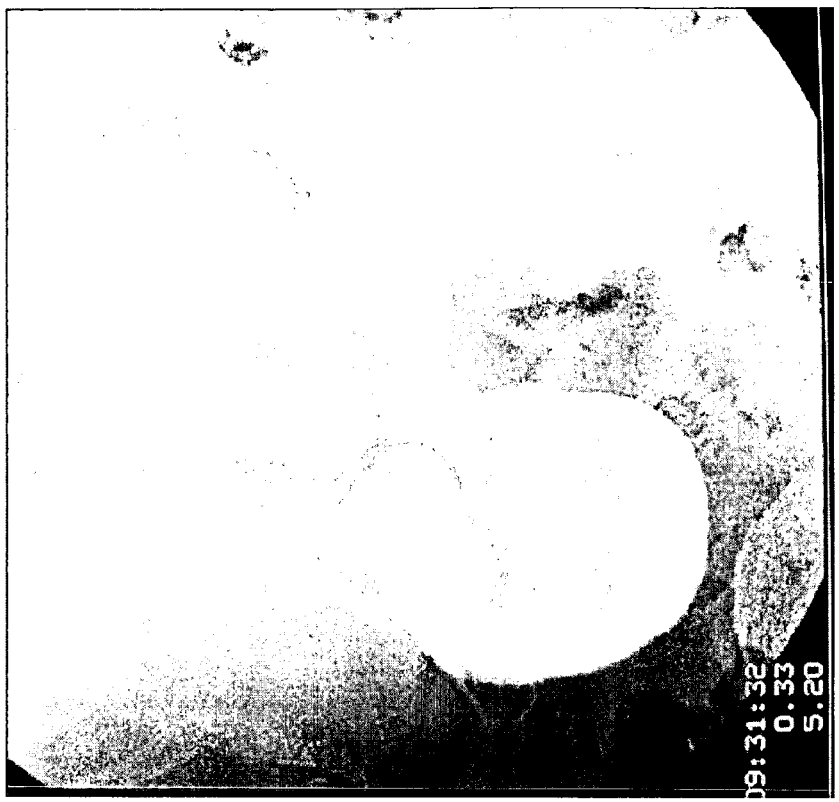
FIG. 7b is a renal angiogram of a renal AVM in the venous phase requiring embolotherapy.
Figure 7A:
FIG. 7a is a renal angiogram of a renal arteriovenous malformation (AVM) in the arterial phase requiring embolotherapy.
Figure 7B:
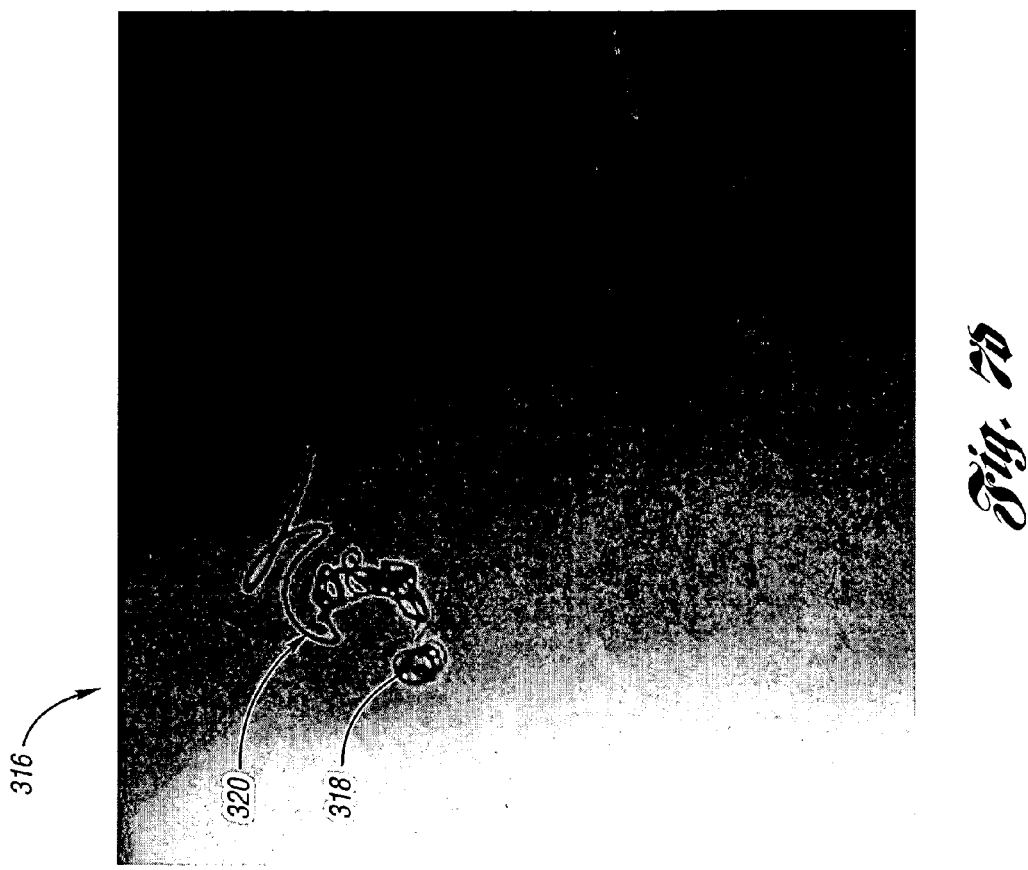
Figure 7C:
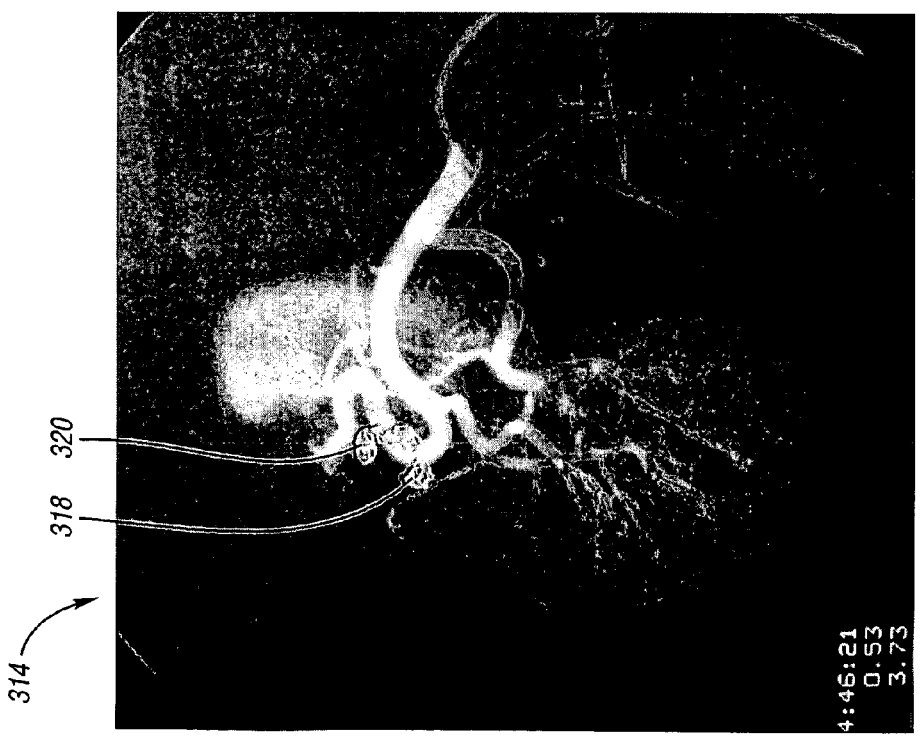
FIG. 7c is a renal angiogram of the renal AVM after embolotherapy with the occluding device.

FIG. 7a is a renal angiogram 310 of a renal AVM in an arterial phase and FIG. 7b is a renal angiogram 312 of a renal AVM in a venous phase. As shown, the renal AVM is an abnormality of dilated tortuous vessels requiring embolotherapy. FIG. 7c is a renal angiogram 314 illustrating successful occlusions of the renal AVM with one embodiment of the occluding device 320 and a conventional embolization coil 318, resulting in a normal appearance of the renal vasculature. FIG. 7d is a renal angiogram 316 illustrating a difference between the conventional embolization coil 318 and one embodiment of the occluding device 320 of the present invention.

Figures 8, 9:
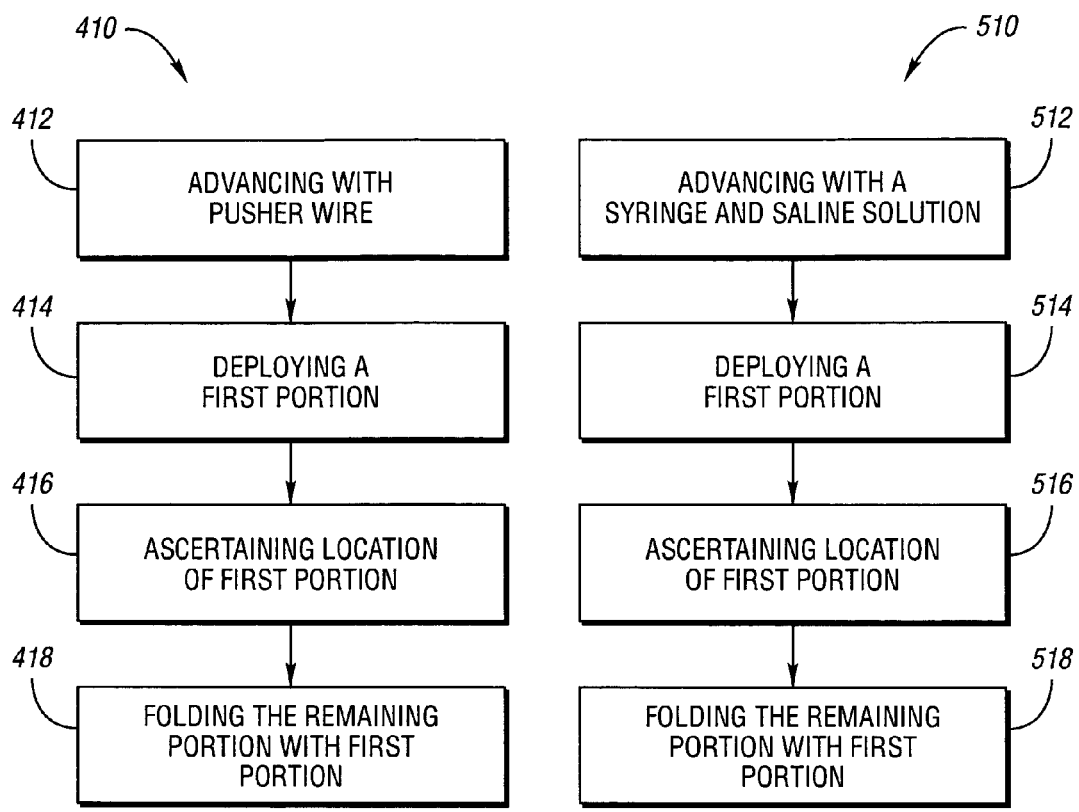
FIG. 8 is a flowchart of a push method for transcatheter embolization of a body vessel.
FIG. 9 is a flowchart of a squirt method for transcatheter embolization of a body vessel.

The occluding device may be deployed in a body vessel by a push embolization method or a squirt embolization method in accordance with the present invention. FIG. 8 illustrates a push embolization method 410 of transcatheter embolization using an embodiment of the occluding device. As typically performed in embolotherapy, an introducer or a guide catheter is percutaneously introduced into the body vessel of a patient and a microcatheter is passed through the guide catheter to position the microcatheter at a desired point of occlusion in the body vessel.

The occluding device, which is elongated to its full length within a cartridge, is loaded in the hub at the proximal end of the microcatheter. In step 412, the device is advanced by the pusher wire in accordance with this method of deploying the occluding device.

In step 414, a first portion of the occluding device, e.g., a first loop of the secondary coil, is deployed at the desired point of occlusion in the body vessel as a remaining portion of the occluding device is held in the microcatheter. The first portion of the coil may be between about 5% to 15% of the length of the coil. In step 416, the location of the first portion in the body vessel is ascertained by any suitable means, such as by fluoroscopy, relative to the body vessel. If the first portion is at the desired point of occlusion in the body vessel, then the first portion is folded across the lumen of the body vessel and the remaining portion of the coil is folded together with the first portion to pack the coil and occlude the body vessel in step 418. FIG. 10a depicts the first portion of the occluding device 10 being packed within a body vessel.

Preferably, the first portion is folded by moving the distal end of the microcatheter against the first portion to fold the first portion across the lumen of the body vessel. The remaining portion is folded onto the first portion by moving the catheter reciprocally back and forth relative to the body vessel as the remaining portion is deployed from the microcatheter. As a length of the remaining portion is being deployed, the distal end of the microcatheter is moved back. The microcatheter is then moved forward against the length of the remaining portion, thereby folding the length of the remaining portion at the desired point of occlusion. The microcatheter is moved back and forth until the remaining portion is folded with the first portion and the occluding device is in a packed state. FIGS. 10b and 10c illustrate the microcatheter 114 being moved forward and back to deploy the remaining portion of the occluding device 10 to pack the coil and occlude the body vessel.

However, if it is ascertained in step 416 that the first portion of the occluding device is not at the desired point of occlusion, then the position of the microcatheter is moved fore or aft relative to the body vessel such that the first portion is placed at the desired point of occlusion.

FIG. 9 illustrates a squirt embolization method 510 of transcatheter embolization using an embodiment of the occluding device of the present invention. As typically performed in embolotherapy, a guide catheter is introduced into the body vessel as described above in the push embolization method. Once the microcatheter is passed through the guide catheter and the occluding device is loaded at the hub of the microcatheter, the occluding device is advanced in step 512 through the microcatheter with use of a luer lock syringe and saline solution. In step 514, a first portion of the occluding device, e.g., a first loop of the secondary coil, is deployed at the desired point of occlusion in the body vessel as a remaining portion of the occluding device is held in the microcatheter. The first portion of the coil may be between about 5% to 15% of the length of the coil.

In step 516, the location of the first portion in the body vessel is ascertained by any suitable means, such as by fluoroscopy, relative to the body vessel. If the first portion of the coil is at the desired point of occlusion in the body vessel, then the remaining portion is folded together with the first portion with the saline solution. Thus, the occluding device is packed across the lumen of the body vessel to occlude the body vessel. FIG. 10a depicts the first portion of the occluding device 10 being packed within a body vessel.

Preferably, the first portion and the remaining portion are folded by moving the distal end of the microcatheter reciprocally back and forth relative to the body vessel as described above. FIGS. 10b and 10c illustrate the microcatheter 114 being moved forward and back to deploy the remaining portion of the occluding device 10 to pack the coil and occlude the body vessel.

However, if it is ascertained in step 516 that the first portion is not at the desired point of occlusion, then the position of the microcatheter is moved fore or aft relative to the body vessel such that the first loop is placed at the desired point of occlusion.

Figure 1C:
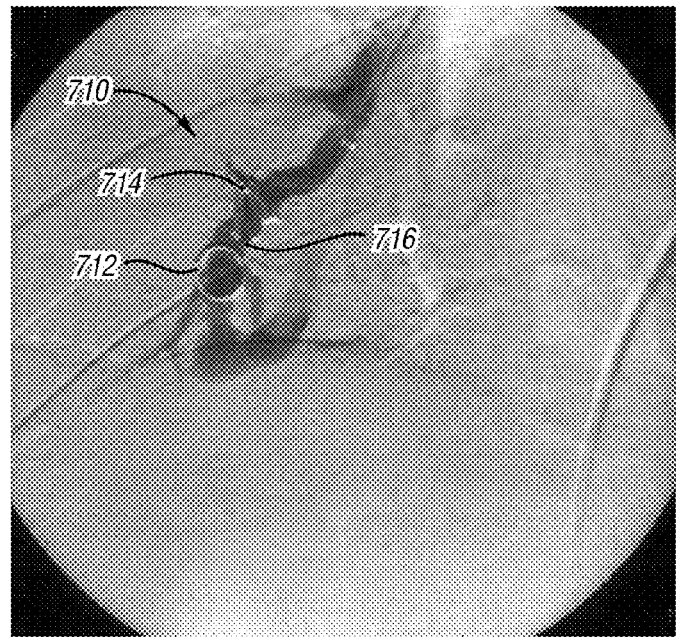
FIG. 1c is a pulmonary angiogram depicting prior art coils in the pulmonary vasculature in the arterial phase.
Figure 1D:
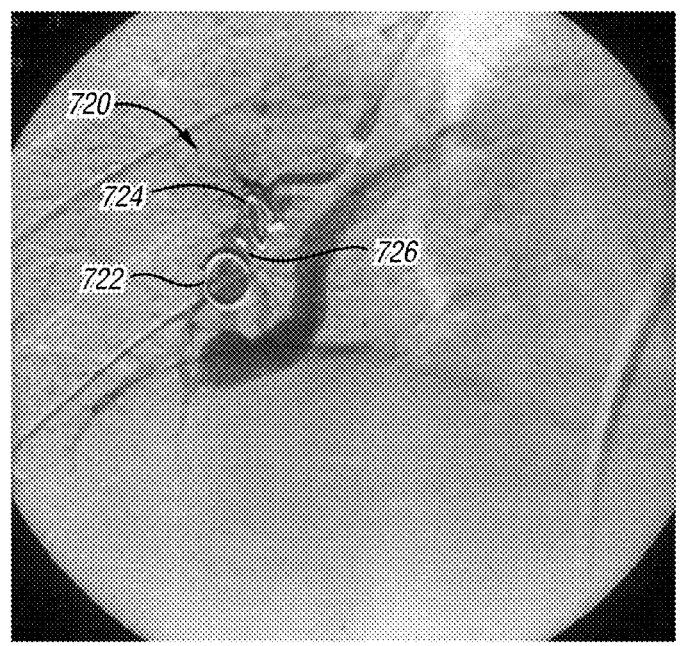
FIG. 1d is a pulmonary angiogram depicting the prior art coils in the pulmonary vasculature in the venous phase.
Figure 11:
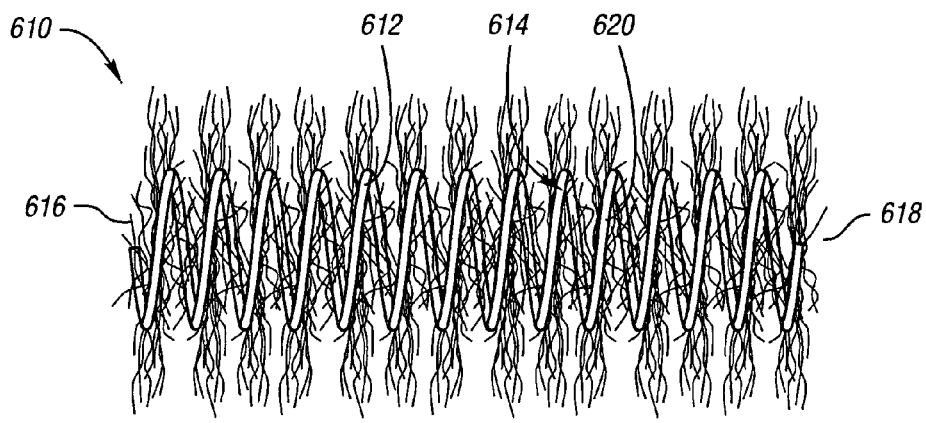
FIG. 11 is another embodiment of the occluding device.

FIG. 11 illustrates an occluding device 610 for occlusion of fluid flow through a body vessel in accordance with another embodiment of the present invention. As shown, the occluding device 610 comprises similar elements as the occluding device 10 described above. For example, the occluding device of 610 includes a secondary coil 612, a secondary body 614, a first end 616, a second end 618, and loops 620 similar to the secondary coil 12, the secondary body 14, the first end 16, the second end 18, and loops 20 of the occluding device 10 in FIG. 1.

In this embodiment, the primary coil 611 has an initial tension of between about 10 and 30 grams of weight. Coil 611 further includes a length of about 3 to 7 centimeters and an outer diameter of between about 0.010 and 0.020 inch. In this embodiment. the microcatheter inner diameter through which the occlusion device may be advanced ranges between about 0.014 to 0.020 inch.

While the present invention has been described in terms of preferred embodiments, it will be understood, of course, that the invention is not limited thereto since modifications may be made to those skilled in the art, particularly in light of the foregoing teachings.

The invention claimed is:

1. An occluding device for occlusion of fluid flow through a lumen of a body vessel, the device comprising:
   a primary coil including a series of first loops and having an initial tension of between about 10 and 30 grams of weight to facilitate the primary coil to be folded in a packed state across the lumen of the body vessel when being deployed, the primary coil being formed into a secondary coil; and fibers attached to the primary coil and extending radially therefrom, the fibers being held between the first loops of the primary coil by the initial tension of the primary coil, the fibers not being looped about turns of the first loops;

wherein the initial tension represents the amount of force necessary to cause a 4 centimeter length of the primary coil to begin to elongate.

2. The device of claim 1 wherein the primary coil is made of platinum.

3. The device of claim 1 wherein the primary coil has a tensile strength of between about 50,000 and 350,000 pounds per square inch.

4. The device of claim 1 wherein the primary coil has a length of between about 3 to 20 centimeters.

5. The device of claim 1 wherein the primary coil has an outer diameter of between about 0.010 to 0.035 inch.

6. The device of claim 1 wherein the secondary coil has an outer diameter of between about 3 to 15 millimeters.

7. The device of claim 1 wherein the secondary coil has a series of second loops, the second loops being axially spaced apart by about 0 to 4 millimeters curl space.

8. The device of claim 1 wherein the fibers are made of a synthetic polyester textile fiber.

9. The device of claim 1 wherein the fibers extend from the primary coil at a length of between about 3 to 8 millimeters, the fibers being comprised of strands having an outer diameter of about 0.00050 to 0.00100 inch.

10. The device of claim 1 wherein the fibers are arranged in strands that are spaced between each other by about 1 to 3 millimeters and extend about 3 to 8 millimeters from the first loops.

11. An occluding device for occlusion of fluid flow through a lumen of a body vessel, the device comprising:

a primary coil formed into a secondary coil, the primary coil having a series of first loops and an initial tension with a ratio of between about 1.25 to 15 grams per centimeter necessary to cause the primary coil to begin to elongate and to facilitate the primary coil being folded across the lumen of the body vessel when being deployed; and fibers attached to the primary coil and extending radially therefrom, the fibers being held between the first loops of the primary coil by the initial tension of the primary coil, the fibers not being looped about turns of the first loops.

12. The device of claim 11 wherein the fibers have strands attached to the primary coil, the strands having a length of between about 3 to 8 millimeters, the strands being spaced apart from each other along the primary coil to occlude fluid flow when deployed.

13. The device of claim 11 wherein the primary coil is made of platinum.

14. The device of claim 11 wherein the primary coil has a length of between about 3 to 20 centimeters.

15. The device of claim 11 wherein the secondary coil has an outer diameter of between about 3 to 15 millimeters.

16. The device of claim 11 wherein the secondary coil has a series of second loops spaced apart by about up to 4 millimeters curl space.

17. The device of claim 11 wherein the fibers are made of synthetic polyester textile fiber.

18. The device of claim 11 wherein the fibers include strands having an outer diameter of about 0.00050 to 0.00100 inch.

19. The device of claim 18 wherein the strands are spaced between each other on the primary coil by about 1 to 3 millimeters.

20. An embolization kit for occluding fluid flow through a body vessel, the kit comprising:

a guide catheter;

a microcatheter having proximal and distal ends and being configured to be passed through the guide catheter to position the microcatheter in the body vessel, the microcatheter having a hub adjacent the proximal end; and an occluding device comprising:

a primary coil including a series of loops and having an initial tension of about 10 to 30 grams of weight to facilitate the primary coil to fold when being deployed, the primary coil being formed into a secondary coil; and fibers attached to the primary coil and extending radially therefrom, the fibers being wedged and held between the loops of the primary coil by the initial tension of the primary coil, the fibers not being looped about turns of the loops;

wherein the initial tension represents the amount of force necessary to cause a 4 centimeter length of the primary coil to begin to elongate.

21. The embolization kit of claim 20 wherein the guide catheter is between about 4-French and 8-French.

22. The embolization kit of claim 20 further comprising a pusher wire for advancing the occluding device.

23. An embolization kit for occluding fluid flow through a body vessel, the kit comprising:

a microcatheter having proximal and distal ends and defining a lumen; and an occluding device comprising:

a primary coil including a series of loops and having an initial tension of about 10 to 30 grams of weight to facilitate the primary coil to fold when being deployed, the primary coil being formed into a secondary coil; and fibers attached to the primary coil and extending radially therefrom, the fibers being wedged and held between the loops of the primary coil by the initial tension of the primary coil, the fibers not being looped about turns of the loops;

wherein the initial tension represents the amount of force necessary to cause a 4 centimeter length of the primary coil to begin to elongate.

24. An occluding device for occlusion of fluid flow through a lumen of a body vessel, the device comprising:

a primary coil including a series of first loops and having an initial tension of about 10 to 30 grams of weight to facilitate the occluding device to be folded in a packed state across the lumen of the body vessel when being deployed, the primary coil being formed into a secondary coil that extends from a proximal end of the primary coil to a distal end of the primary coil; and fibers attached to the primary coil and extending radially therefrom, the fibers being wedged and held between the first loops of the primary coil by the initial tension of the primary coil;

wherein the initial tension represents the amount of force necessary to cause a 4 centimeter length of the primary coil to begin to elongate.

* * * * *